United States Patent [19]

Schroeppel

[11] Patent Number: 4,651,740

[45] Date of Patent: Mar. 24, 1987

[54] IMPLANT AND CONTROL APPARATUS AND METHOD EMPLOYING AT LEAST ONE TUNING FORK

[75] Inventor: Edward A. Schroeppel, Miramar, Fla.

[73] Assignee: Cordis Corporation, Miami, Fla.

[21] Appl. No.: 703,134

[22] Filed: Feb. 19, 1985

[51] Int. Cl.⁴ .............................................. A61N 1/00
[52] U.S. Cl. ............................... 128/419 P; 367/191; 181/139
[58] Field of Search ............ 128/1 R, 419 P, 419 PG, 128/419 PS, 419 PT, 419 R, 903, 904; 367/191; 181/139

[56] References Cited

U.S. PATENT DOCUMENTS

| | | | |
|---|---|---|---|
| 3,672,352 | 6/1972 | Summers | 128/2 R |
| 3,830,242 | 8/1974 | Greatbatch | 128/419 PT |
| 4,041,954 | 8/1977 | Ohara | 128/419 PT |
| 4,082,097 | 4/1978 | Mann et al. | 128/419 PS |
| 4,124,031 | 11/1978 | Mensink et al. | 128/419 PG |

Primary Examiner—William E. Kamm
Attorney, Agent, or Firm—Henry W. Collins; Thomas R. Vigil

[57] ABSTRACT

The apparatus and method are utilized in controlling an implanted device, such as a cardiac pacer, by use of acoustic vibrations generated by a tuning fork. These vibrations are applied externally to the skin overlying the implanted device and are sensed by a transducer within the implanted device. The transducer generates an electrical signal of a frequency correlated to the tuning fork frequency. An amplifier and tuned filter are utilized to detect predetermined frequencies within the electrical signals produced by the transducer and to direct the processed signals to a programmable electronic device for control of the implanted device.

21 Claims, 8 Drawing Figures

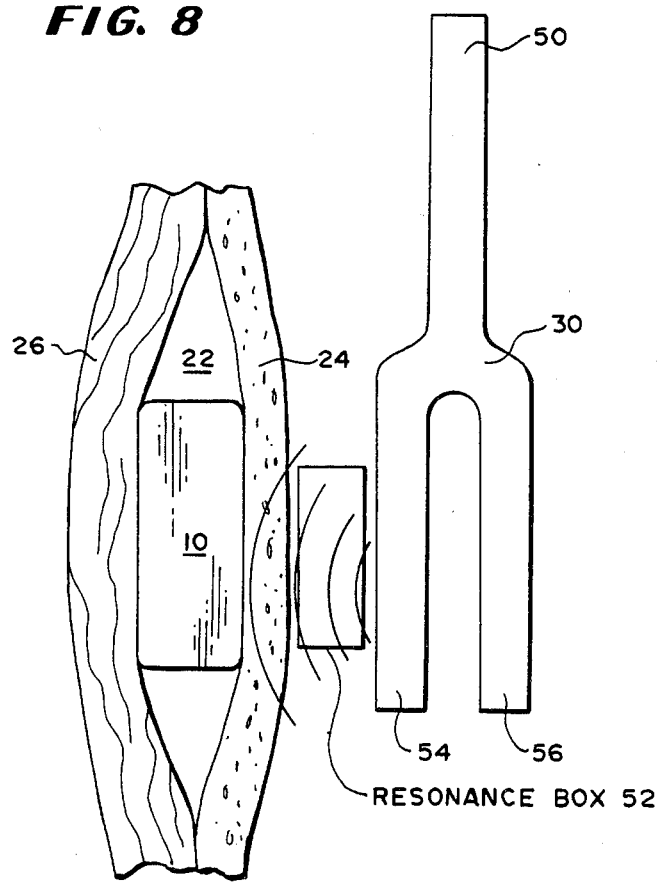

IMPLANT AND CONTROL APPARATUS AND METHOD EMPLOYING AT LEAST ONE TUNING FORK

BACKGROUND OF THE INVENTION

1. Field of the Invention

The present invention relates generally to methods for changing internal parameters of implanted devices, such as a cardiac pacemaker, and more particularly to means, such as the use of a vibration generating external device, for generating a programmed response within the implant.

2. Description of the Prior Art

Prior methods for controlling or changing the parameters of an implanted cardiac pacemaker have included the application of a permanent magnet wherein the magnetic field generated causes a magnetic reed switch within the pacemaker to close. This actuation of the magnetic reed switch is then used to activate or deactivate a circuit or to set parameters within the pacemaker. As an example, an output generated by a circuit which is generally inhibited when cardiac activity exceeds a preset rate can be converted by application of the magnet to an output which stimulates cardiac rate at a preset value.

In another method, an external programming device generates pulsating magnetic fields and coded signals which are transmitted to a reed switch within the implanted cardiac pacer. The signal is then decoded by the implanted pacer through detection of the repetitive actuation of the reed switch and provides, in a programmed response thereto, a set of parameters within the implanted pacer. An example would be to change a cardiac pacer from atrial pacing to ventricular pacing or from atrial fixed-rate pacing to atrial inhibited pacing or to change the cardiac stimulating current from 7 milliamps to 5 milliamps.

Although no implant systems responsive to vibration control are known to applicants, prior references using vibration signals have been proposed. In particular, the Summers U.S. Pat. No. 3,672,352 discloses a system for monitoring a condition of a body function or organ or of a device implanted within a body and includes an implanted sensor or transducer connected to a signal generating device. This signal generating device is arranged to generate an audible, visual or heat signal representing the condition of the implanted device, as, for example, the status of the battery charge. More particularly, this signal generating device uses a variation in intensity, such as an on/off code, to transmit information about the condition of the implanted device through the skin to a signal receiver.

Another system is proposed in the Mann U.S. Pat. No. 4,082,097 which presents a system for controlling the charging of an implanted battery. In this patent it is suggested that the battery recharging could be accomplished through the transmission of energy through the skin of the patient. This transmission was described in terms of electromagnetic fields but suggested the possibility that mechnical vibrating waves from an external source could be used to penetrate the skin and recharge the battery.

A similar system is proposed in the O'3 Hara U.S. Pat. No. 4,041,954. Here an electromagnetic generator or a mechanical sound wave generator is utilized to project energy into an implanted receiver which thereupon generates an information signal for external transmission.

SUMMARY OF THE INVENTION

According to the invention there is provided an implanted device whose parameters can be non-invasively changed by the use of acoustic vibrations of relatively pure frequencies such as those generated by a tuning fork. In its simplest configuration, the device is implanted within the patient and has a circuit designed to respond to one frequency. These acoustic vibrations are converted by the transducer into electrical signals which can then be transmitted through an electrical signal amplifier to a tuned filter for selection of the peak signal for processing in a processing circuit. The processing circuit then causes a response such as, for example, switching the pacer from the inhibited mode to a fixed rate pacing mode at a preset rate.

There is further provided according to the invention a method of controlling an implanted device by applying a vibrating tuning fork directly adjacent the skin overlying the implanted device such as a pacer. A frequency selective detector in the pacer can then respond and select a desired function according to programming. By using two or more detectors and two or more tuning forks at different frequencies, different functions may then be initiated. Alternatively, tuning forks could be applied in a coded sequence. Since tuning forks generate relatively pure frequencies, difficulties with environmental interference would be minimized.

A tuning fork actuated system poses extraordinary potential since tuning forks are readily available, require no power supply, are transportable, safe and easy to use. They are also standardized and generally inexpensive. Further, certain frequencies can be standardized for programming standardized operation, i.e., frequency "A" can be used for programming the pacer into a recognized safe operation; frequency "B" can be used to initiate a "dump" of information held within the implant, and frequency "C" can be used to generate an emergency operation, such as to terminate a tachycardia episode. Outside the field of pacers, this method of controlling an implanted device can be used to control the type or quantity of a drug to be delivered by an implanted drug delivery system. Moreover, this tuning fork method of controlling an implant can be used together with an electromagnetic control system to provide increased security for the implanted device whereby predetermined combinations of the magnet and tuning fork can be used to accomplish objectives.

Generally the method of operation employs the selection of a tuning fork at the appropriate frequency corresponding to the frequency of the tuning filter within the circuitry of the implant. A physician strikes the tuning fork against a table or other hard surface to generate the tuning fork frequency. The vibrating tuning fork is then held over the skin of the patient proximate the implanted device and acoustic vibrations are caused to penetrate the tissue and be received by the implanted device. These acoustic vibrations are then detected by the transducer, amplified and filtered, and finally received by the processing circuitry whereupon an appropriate programmed mode is initiated.

BRIEF DESCRIPTION OF THE DRAWINGS

FIG. 8 illustrates a modified form of the FIG. 4 device using a resonance box.

DESCRIPTION OF THE PREFERRED EMBODIMENT

Figure 1:
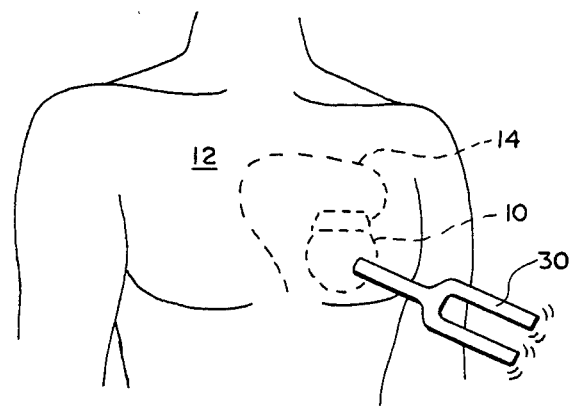
FIG. 1 illustrates a diagram of a cardiac pacer implanted within the body of a patient and shows a tuning fork positioned near the skin over the implanted pacer.

Referring now to FIG. 1 there is illustrated therein a cardiac pacer 10 implanted within a body 12 of a patient. Although the following remarks are directed primarily toward the use of an implanted cardiac pacer 10, the principles and means used to accomplish the invention are equally applicable to the control of other implanted devices. Inasmuch as FIG. 1 depicts a cardiac pacer, there is further shown for reference a pervenous lead 14 extending from the cardiac pacer 10 for connection to the heart muscle (not shown).

Figure 2:
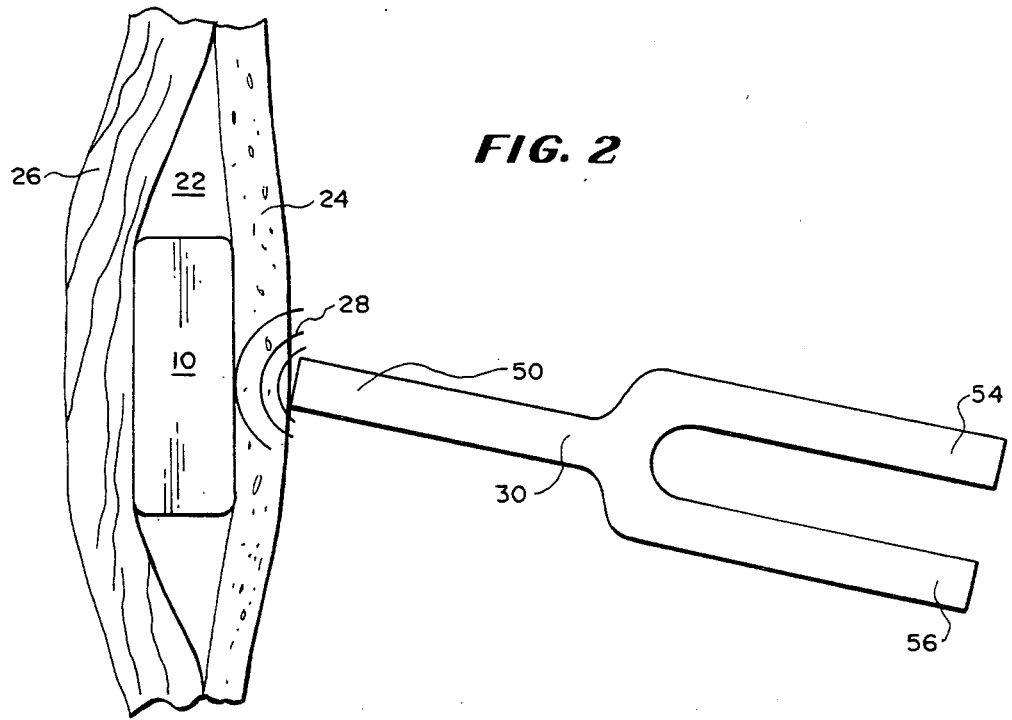
FIG. 2 illustrates a cardiac pacer implanted in a subcutaneous pocket formed between the skin and muscle and shows acoustic vibrations being transmitted through the skin to the cardiac pacer.

As shown in FIG. 2, this pacer 10 can be arranged and positioned in a pocket 22 formed between the skin 24 and the muscle 26 of a patient.

In accordance with one preferred embodiment of the present invention, this cardiac pacer 10 is arranged to respond in a preprogrammed manner to the application of acoustic vibrations 28 impinged thereon. These vibrations are preferably generated by a pure frequency device, such as a tuning fork 30 and are transmitted through the skin 24 to the pacer 10.

Figure 3:
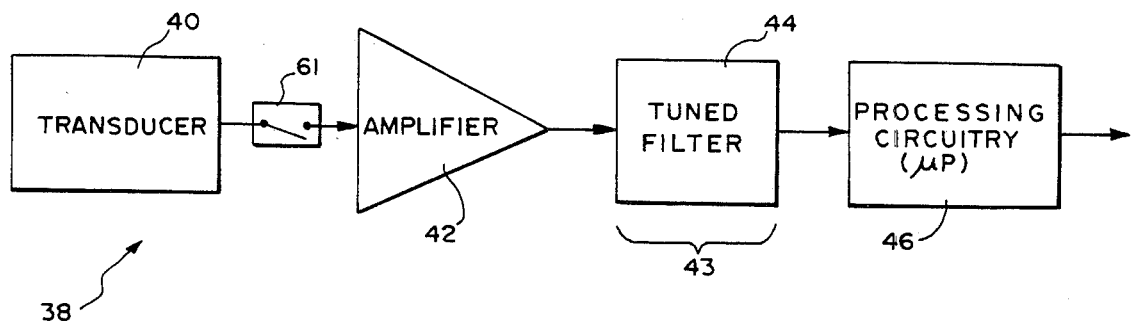
FIG. 3 is a block circuit diagram of the pacer circuitry of the present invention mounted within the implanted cardiac pacer and shows a mechanical-electrical transducer for detecting the tuning fork vibrations, an amplifier, a tuned filter and processing circuitry.

Turning now to FIG. 3, there is shown therein a block circuit diagram of an electrical circuit 38 mounted in the pacer 10 for carrying out the teachings of the present invention. The circuit 38 is mounted within the cardiac pacer 10 or other implanted device. In its simplest configuration, the circuit 38 is designed to respond to a single frequency. In this respect an incoming vibration from the tuning fork 30 is reduced to an electrical signal by a transducer 40, amplified by an amplifier 42 and then fed to a frequency selection circuit 43 comprising a tuned filter 44 for actuation of processing circuitry 46. More particularly, the transducer 40 converts the impinging acoustic vibrations 28 into corresponding electrical signals.

In practice, this transducer 40 would be a microphone or piezoelectric element. The electrical signals from the transducer 40 are then amplified by the amplifier 42 and fed directly to a tuned filter 44. This tuned filter 44 represents electrical circuitry designed to select the peak signal and its corresponding frequency and to transmit the chosen frequency electrically to the processing circuitry 46. This processing circuitry 46 is generally a programmable electronic device, such as a microprocessor, arranged to respond in a programmed manner to preselected frequencies.

The purpose of the tuned filter 44 may be further explained by reference to the expected noise or unwanted signals which may be processed through the transducer and amplifier. Generally speaking, extraneous frequencies may be processed but will not represent a pure frequency, while the tuned filter 44 is designed to select a predetermined pure frequency. Acting upon the electrical signal generated in response to the acoustical vibrations, the tuned filter 44 is designed to detect the electrical signal having a large component correlated with the desired pure frequency. The strong presence of other unwanted frequencies would result in a negative response by the circuitry 43. Thus, there must be present a single frequency of sufficiently large components in order to cause a parameter change within the implanted pacer 10.

The basic operation of the circuitry 38 of the present invention is initiated after implantation when a change in parameters in the implanted pacer 10 is required or at some other appropriate time for test purposes. A tuning fork 30 which correlates with the frequency to which the tuned filter 44 has been set is chosen and is caused to vibrate. A single member end 50 (as shown in FIGS. 1 and 2) is then held against the skin 24 of the patient 12 over the implanted cardiac pacer 10. The mechanical vibrations resulting from vibration of the single member end 50 are caused to emanate from the tuning fork 36 and are transmitted through the skin 24 to the cardiac pacer 10. Impedance matching may be facilitated by using a resonance box 52 which is positioned between the tuning fork 30 and the patient as shown in FIG. 8.

Figure 4:
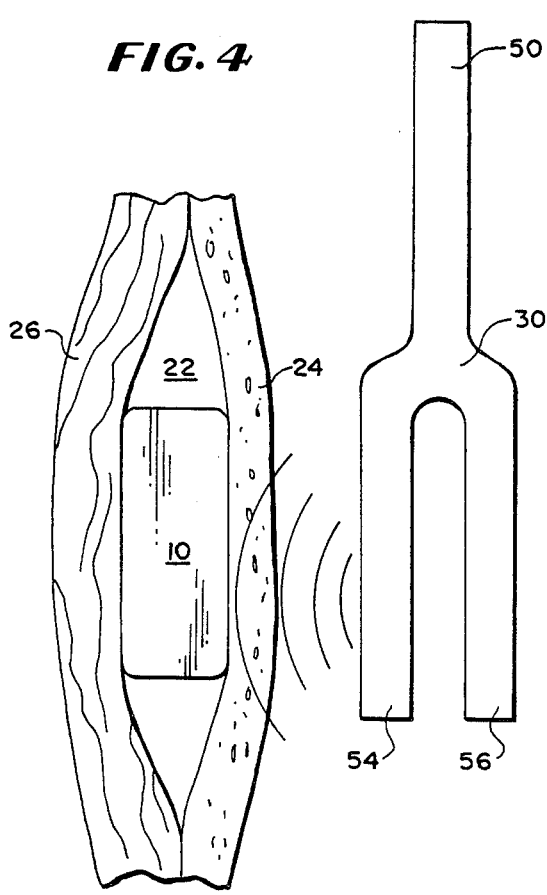
FIG. 4 illustrates the cardiac pacer implanted in a subcutaneous pocket between the skin and muscle whereby the tuning fork is applied in a second mode of operation.

In an alternative form of operation, as shown in FIG. 4, the tuning fork 30 is arranged so that forked ends 54, 56 are positioned over the skin adjacent to the implanted cardiac pacer 10. Similarly, in this position, the acoustic vibrations are transmitted across the air layer between the tuning fork 30 and the skin 24, through the skin 24, and to the cardiac pacer 10.

In either mode of operation, the vibrations reaching the cardiac pacer 10 are sensed by the transducer 40 and reduced to electrical signals thereby, amplified and fed to the tuned filter 44 where the frequency selection process takes place. The processing circuitry 46 is electrically coupled to the output of the tuned filter 44 and programmed to respond to the detected signals passed through the tuned filter 44.

A typical application of the basic operation would involve programming a cardiac pacer 10 to "stat" parameters. In such an instance, the programmable circuitry 46 would be designed to respond to the detection of a predetermined frequency and to respond by programming the cardiac pacer to the "stat" parameters. In the instance of a tachycardia episode, a rapid burst of electrical pulses from the cardiac pacer 10 can be used to treat such condition. In such an instance, a tuning fork 30 generated vibrating signal would be applied near the skin 24 over the cardiac pacer 10 containing the transducer 40 and tuning filter circuitry 43. The vibrations would then be processed through the transducer 40, amplified, and the peak frequency selected by the tuned filter 44 and fed to the programmed electronic circuitry 46.

Upon receipt of the predetermined frequency, the programmed electronic circuitry 46 will select a set of parameters to cause the pacer 10 to generate a rapid burst of electrical pulses to disrupt the tachycardia episode and would then subsequently reprogram the cardiac pacer 10 to the "stat" parameters.

Figure 5:
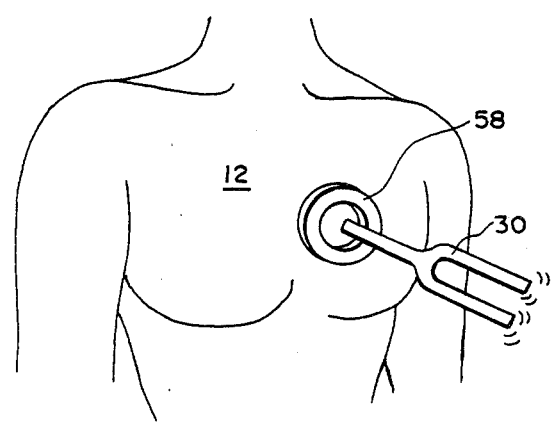
FIG. 5 illustrates the application of a tuning fork and a permanent magnet in yet a further method employing the tuning fork actuated circuitry of the present invention.

In yet a further embodiment of the present invention, additional security for the device can be incorporated by utilizing a magnetic switch. As shown in FIG. 5, the application of a permanent magnet 58 near the skin overlying the cardiac pacer 10 can be used to close a magnetic reed switch generally identified by reference numeral 61 in FIG. 3 connected in series between transducer 42 and amplifier 42, or generally identified by reference numeral 63 connected to the processing circuitry 70 in FIG. 6 in the pacer 10. This closure of the reed switch can be used to convert the cardiac pacer 10 to a preset mode of operation, or to enable the cardiac pacer 10 for transmission of the mechanical vibrations through the skin 24 into the pacer 10 whereupon the implanted transducer 40 responds thereto. This application of the tuning fork 30 can be arranged to change other parameters of the cardiac pacer 10 such as sensitivity, rate, output, or to initiate a sequential change of parameters according to a preprogrammed sequence. The programming circuitry 46 can be arranged to place the cardiac pacer 10 into a preprogrammed mode on removal of the tuning fork 30.

Figure 6:
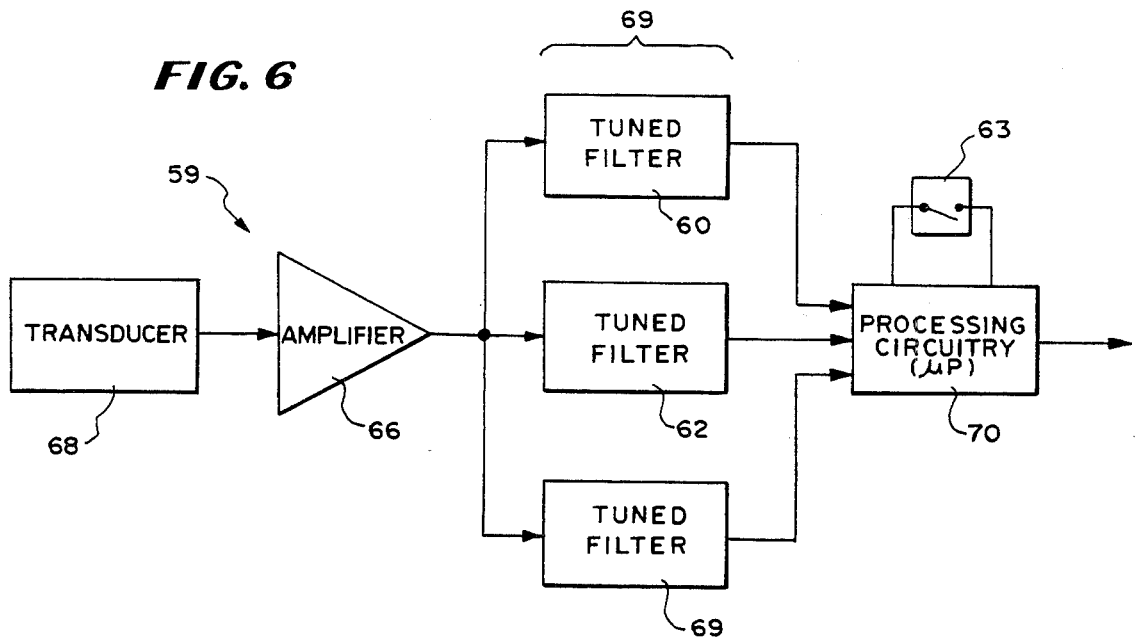
FIG. 6 is a block circuit diagram of the pacer circuitry of another embodiment of the present invention in which three tuned filters are utilized, each tuned to a different frequency.

Turning now to FIG. 6, there is shown a block circuit diagram of another embodiment of the control circuitry of the present invention. This circuitry is identified generally with reference numeral 59 and includes a plurality of (three) tuned filters 60, 62 and 64. Each tuned filter 60, 62 and 64 is electrically coupled to the output of an amplifier 66 as in the previously described circuitry 38. The input to this amplifier 66 comes from a mechanical to electrical transducer 68. As before, this transducer 68 can be a microphone or piezoelectric element arranged to receive the pure frequency mechanical vibrations from the tuning fork 30 and to generate an electrical signal correlated thereto. The signal is then fed to the amplifier 66 and, once amplified, to the bank 69 of tuned filters 60, 62 and 64.

Upon application of a plurality of frequency inputs to the transducer 68, a plurality of correlated frequencies will be presented to the tuned filter bank 69. With each tuned filter 60, 62 and 64 tuned to a different frequency, programmed processing circuitry 70 can be arranged to respond to the separate output of each.

Accordingly, a multitude of parameter changes can be initiated by the programmed processing circuitry 70 in response to the combinations of frequencies detected by the tuned filter bank 69. Moreover, the programmed processing circuitry 70 can be arranged to respond to a coded array of simultaneously input frequencies and to generate a preprogrammed pattern of parameters in response thereto or, either in the alternative or in combination therewith, to respond to a predetermined sequence of predetermined frequencies.

Figure 7:
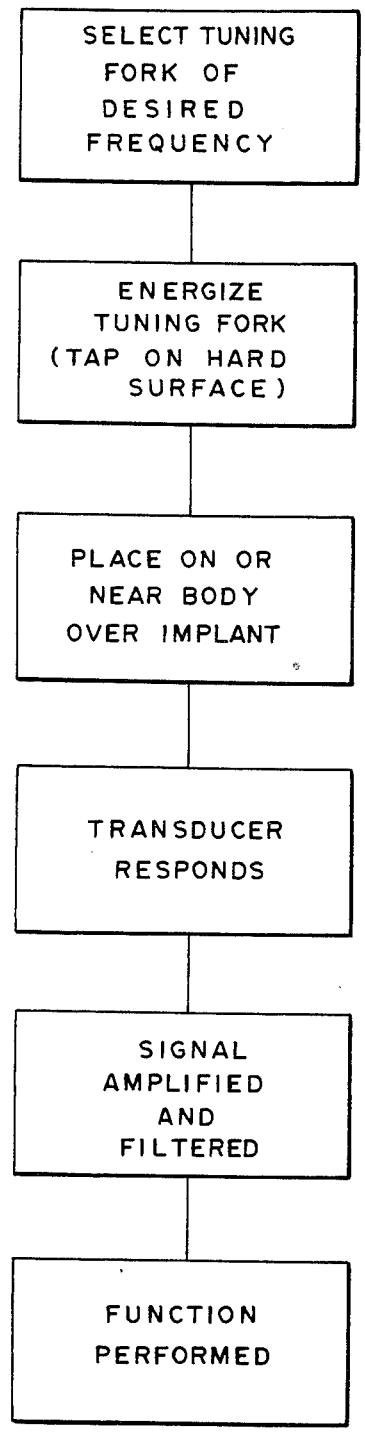
FIG. 7 is a flow chart of the operation sequence of the pacer circuitry of the present invention.

In summary, the general function and method of the present invention may be clearly understood by reference to FIG. 7 depicting a flow diagram of the signal processing protocol carried out with the implanted pacer 10.

First, depending on the programming of the programmable electronic device and the parameters desired to be generated by the programmable device, the operator selects a tuning fork 30 or other pure frequency generator of the desired frequency.

Next he activates or energizes the tuning fork 30 which in its simplest mode merely requires a tap on a hard surface.

As a next step, the frequency generating device or tuning fork 30 is placed on or near the skin 24 overlying the implanted device, e.g. pacer 10, in a manner arranged to direct the mechanical vibrations through the skin 24 to the circuitry 38 or 59.

As a further step, the transducer 40 or 68 of the circuitry 38 or 59 is arranged to respond to the incoming mechanical vibration and to generate electrical signals correlating thereto.

The signal generated by the transducer is then caused to be processed through an amplifier and fed to one or more tuned filters for frequency selection in the next step.

Finally, selected signal or signals filtered by the frequency selection circuitry comprising the tuned filters are received by the programmed electronic processing circuitry 46 or 70 which is arranged to respond to the incoming frequencies and provide responsive changes in control parameters for the implanted device 10.

From the foregoing description it will be apparent that modifications can be made to the apparatus of the present invention and method for using same without departing from the teachings of the present invention. Accordingly, the scope of the invention is only to be limited as necessitated by the accompanying claims.

I claim:

1. A method for controlling the operation of a device implanted beneath the skin of a patient, said method comprising the steps of:
    generating at least one predetermined pure frequency acoustic signal with at least one tuning fork;
    placing the tuning fork generating said signal externally near the skin overlying the implanted device;
    transducing the acoustic signal in the device to an electrical signal;
    filtering the electrical signal;
    supplying the filtered electrical signal to signal processing circuitry; and
    utilizing said filtered signal to cause said implanted device to perform a certain function.

2. The method of claim 1 wherein the step of placing the tuning fork comprises placing the single end of the tuning for adjacent the skin overlying the implanted device.

3. The method of claim 1 wherein the step of placing the tuning fork comprises placing the forked end of the tuning fork adjacent the skin overlying the implanted device.

4. The method of claim 1 including the step of amplifying said electrical signal prior to filtering same.

5. The method of claim 1 including the step of establishing a magnetic field adjacent the patient's skin in conjunction with the generating of said pure frequency acoustic signal; and utilizing said magnetic field in the implanted device to permit reception of said acoustic signal by the implanted device.

6. The method of claim 1 including the steps of:
    generating a plurality of predetermined pure frequency acoustic signals;
    transducing each acoustic signal to an electrical signal;
    filtering each signal;

supplying each signal to the signal processing circuitry; and utilizing said filtered signal to cause said implanted device to perform another function.

7. A method for controlling the operation of a device which is implanted beneath the skin of a patient and which includes an acoustic vibration to electrical signal transducer, at least one electrical tuned filter coupled to the transducer for detecting a signal of a predetermined frequency, and a programmable electronic device coupled to the output of the at least one tuned filter for decoding the frequency signal received from the filter and for initiating a response, said method comprising the steps of: placing a vibrating tuning fork externally near the skin overlying the implanted device; and causing the output of the programmable electronic device to respond only to a signal related to the frequency of the tuning fork generated acoustic signal.

8. A method for controlling the operation of a device which is implanted beneath the skin of patient and which includes an acoustic vibration-to-electrical signal transducer, a plurality of electrical tuned filters coupled to said transducer for detecting frequencies, and a programmable electronic device coupled to said tuned filters for decoding signals and initiating responses, comprising the steps of:

placing a plurality of vibrating tuning forks externally near the skin overlying the implanted device, and causing the output of the programmable electronic device to respond to a combination of signals related to the frequencies of the tuning fork generated acoustic signals from the plurality of tuning forks placed over the implanted device.

9. A method for controlling the operation of a device which is implanted beneath the skin of a patient and which includes an acoustic vibration to electrical signal transducer, a plurality of electrical tuned filters coupled to said transducer for detecting frequencies, and a programmable electronic device coupled to said tuned filters for decoding signal and initiating responses, comprising the steps of:

placing a plurality of vibrating tuning forks in succession near the skin overlying the implant, and causing the output of the programmable electronic device to respond to a predetermined order of signals related to the preselected frequencies of the tuning fork generated acoustic signals.

10. A method for controlling the operation of a device which is implanted beneath the skin of a patient and which includes a magnetically operable switch, an acoustic vibration-to-electrical signal transducer, a plurality of electrical tuned filters coupled to said transducer for detecting frequencies, and a programmable electronic device coupled to said tuned filters for decoding signals and initiating responses of implant control parameters, comprising the steps of:

magnetically closing said magnetically operable switch;

causing the output of the programmable electronic device to respond to said closing of said magnetically operable switch;

placing a vibrating tuning fork externally near the skin overlying the implanted device; and causing the output of the programmable electronic device to respond only to a predetermined signal relative to the frequency of the tuning fork generated acoustic signal.

11. The method of claim 10 wherein said step of causing the output of the programmable electronic device to respond to the closing of the magnetically operable switch includes placing the implanted device in a predetermined mode of operation, and said step of causing the output of the programmable electronic device to respond to the application of the tuning fork includes causing the implant control parameters to cycle through a preset sequence of parameters and causing the implanted device to retain the current parameter upon removal of the tuning fork.

12. A method for controlling the operation of a device which is implanted beneath the skin of a patient and which includes a magnetically operable switch, an acoustic vibration-to-electrical signal transducer; a plurality of electrical tuned filters coupled to said transducer for detecting frequencies, and a programmable electronic device coupled to said tuned filters for decoding signals and initiating response of implant control parameters comprising the steps of:

magnetically closing said magnetically operable switch;

causing the output of the programmable electronic device to respond to said closing of said magnetically operable switch;

placing a plurality of vibrating tuning forks externally near the skin overlying the implanted device, and causing the output of the programmable electronic device to respond to signals related to the predetermined frequencies of the tuning fork generated acoustic signals.

13. A method for controlling the operation of a device which is implanted beneath the skin of a patient and which includes a magnetically operable switch, an acoustic vibration-to-electrical signal transducer, a plurality of electrical tuned filters coupled to said transducer for detecting frequencies, and a programmable electronic device coupled to said tuned filters for decoding signals and initiating response of implant control parameters, comprising the steps of:

magnetically closing said magnetically operable switch;

causing the output of the programmable electronic device to respond to said closing of said magnetically operable switch;

placing a plurality of vibrating tuning forks in succession near the skin overlying the implanted device; and causing the output of the programmable electronic device to respond to a predetermined order of signals related to the frequencies of the tuning fork generated acoustic signals.

14. The method of claim 13 wherein said step of causing the programmable electronic device to respond to the closing of the magnetically operable switch includes placing the implanted device in a predetermined mode of operation, and said step of causing the programmable electronic device to respond to the application of the tuning fork includes causing the implant control parameters to cycle through a preset sequence and causes the implanted device to retain the current parameter upon removal of the tuning fork.

15. A system including a tuning fork and an apparatus which is adapted to be implanted in a body and which is responsive to acoustic signals of a relatively pure frequency generated outside the body in which the apparatus may be implanted, said apparatus comprising:

an acoustic transducer responsive to low energy sound vibrations generated by said tuning fork and providing an electrical signal corresponding in frequency and amplitude to the sound vibrations;

filter means including at least one tuned filter for receiving an electrical signal originated from said acoustic transducer and only transmitting those signals of preselected frequencies;

an amplifier coupled between said transducer and said filter means for increasing the strength of an electrical signal originating from said acoustic transducer; and control means for receiving signals transmitted through said filter means and altering the function of the implantable apparatus in response to the transmitted signals.

16. The apparatus of claim 15 wherein said filter means transmit signals of a single preselected frequency.

17. The apparatus of claim 15 wherein said filter means comprise a plurality of tuned filters, each transmitting a signal of a single preselected frequency which differs from the single preselected frequency transmitted by another tuned filter.

18. The apparatus of claim 15 including a magnetically responsive switch coupled to said aparatus and responsive to a static magnetic field for enabling said apparatus to receive signals transmitted through said filter means to said control means.

19. The apparatus of claim 15 further including a magnetically responsive switch coupled to said apparatus and responsive to a static magnetic field for enabling the alteration of the function of the implantable apparatus in response to the transmitted signals received by such control means.

20. A system including a plurality of tuning forks and an apparatus which is adapted to be implanted in a body and which is responsive to acoustic signals of a relatively pure frequency generated outside the body in which the apparatus may be implanted, an acoustic transducer responsive to low energy sound vibrations generated by any one of said plurality of tuning forks and providing an electrical signal corresponding in frequency and amplitude to the sound vibrations;

filter means for receiving an electrical signal originated from said acoustic transducer and only transmitting those signbals of preselected frequencies, said filter means comprising a plurality of tuned filters equal in number to said plurality of tuning forks, each transmitting a signal of a single preselected frequency which differs from the single preselected frequency transmitted by another tuned filter;

an amplifier coupled beween said transducer and said filter means to increase the strength of an electrical signal originating from said acoustic transducer; and control means for receiving signals transmitted through said filter means and altering the function of the implantable apparatus in response to the transmitted signals.

21. The apparatus of claim 20 further including a magnetically responsive switch coupled to said apparatus and responsive to a static magnetic field for enabling said apparatus to receive signals transmitted through said filter means to said control means.

* * * * *